United States Patent
Turkson et al.

(10) Patent No.: US 8,969,578 B2
(45) Date of Patent: Mar. 3, 2015

(54) INHIBITORS OF STAT3

(75) Inventors: James Turkson, Orlando, FL (US); Andrew D. Hamilton, Guilford, CT (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 675 days.

(21) Appl. No.: 13/119,575

(22) PCT Filed: Sep. 17, 2009

(86) PCT No.: PCT/US2009/057291
§ 371 (c)(1),
(2), (4) Date: May 26, 2011

(87) PCT Pub. No.: WO2010/033685
PCT Pub. Date: Mar. 25, 2010

(65) Prior Publication Data
US 2011/0223661 A1  Sep. 15, 2011

Related U.S. Application Data

(60) Provisional application No. 61/097,693, filed on Sep. 17, 2008.

(51) Int. Cl.
*C07D 263/00* (2006.01)
*C07D 277/00* (2006.01)
(Continued)

(52) U.S. Cl.
CPC ............ *C07D 263/34* (2013.01); *C07D 277/56* (2013.01); *C07F 9/12* (2013.01); *C07F 9/653* (2013.01); *C07F 9/6539* (2013.01)
USPC ........... 548/100; 548/215; 548/146; 435/375; 514/92

(58) Field of Classification Search
None
See application file for complete search history.

(56) References Cited

U.S. PATENT DOCUMENTS

2011/0124602 A1 * 5/2011 Turkson et al. ................. 514/92

FOREIGN PATENT DOCUMENTS

| CA | 2737360 | 9/2009 |
|----|---------|--------|
| EP | 09815184 | 9/2009 |

(Continued)

OTHER PUBLICATIONS

Siddiquee, KA et al "An Oxazole-Based Small-Molecule Stat3 Inhibitor Modulates Stat3 Stability and Processing and Induces Antitumor Cell Effects" Chem. Bio., Dec. 21, 2007, 12(2), pp. 787-798.*

(Continued)

*Primary Examiner* — Jon P Weber
*Assistant Examiner* — Aaron J Kosar
(74) *Attorney, Agent, or Firm* — Ballard Spahr LLP

(57) ABSTRACT

Disclosed herein are compounds derived from a chemical structure according to the formula (I) wherein X comprises oxygen or sulfur, $R^1$ comprises a phenyl or naphthyl group, $R^2$ comprises an amide group and $R^3$ comprises a phosphate group. The disclosed compounds demonstrate inhibitory activity against STAT3, a protein found in certain tumor tissues and which promotes cellular overproliferation and resistance to apoptosis. The invention includes compositions containing the disclosed compounds, as well as methods of treatment therewith.

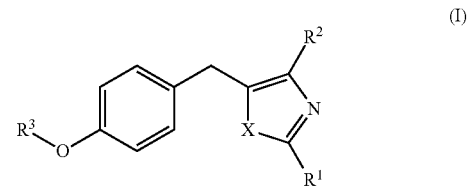

42 Claims, 4 Drawing Sheets

(51) Int. Cl.
| | |
|---|---|
| A61K 31/41 | (2006.01) |
| A61K 31/421 | (2006.01) |
| A61K 31/426 | (2006.01) |
| C07D 263/34 | (2006.01) |
| C07D 277/56 | (2006.01) |
| C07F 9/12 | (2006.01) |
| C07F 9/653 | (2006.01) |
| C07F 9/6539 | (2006.01) |
| C07D 291/00 | (2006.01) |
| C12N 5/00 | (2006.01) |
| A61K 31/381 | (2006.01) |

(56) References Cited

FOREIGN PATENT DOCUMENTS

| WO | WO 2008/070697 | 6/2008 |
|---|---|---|
| WO | WO 2008070697 A2 * | 6/2008 |
| WO | WO 2010/033685 | 3/2010 |

OTHER PUBLICATIONS

Cummings, CG and Hamilton, AD "Expedient route to functionalized and water soluble 5-6-5 imidazole-phenyl-thiazole based .alpha.-helix mimetics" Tetrahedron, 2013, 69(5), pp. 1663-1668.*
Alas S, et al. (2003) Inhibition of constitutive STAT3 activity sensitizes resistant non-Hodgkin's lymphoma and multiple myeloma to chemotherapeutic drug-mediated apoptosis. Clin Cancer Res. 9: 316-326.
Boger DL, et al. (2001) A simple, high-resolution method for establishing DNA binding affinity and sequence selectivity. J Am Chem Soc. 123: 5878-5891.
Bromberg, J. (2002) STAT proteins and oncogenesis. J Clin Invest. 109: 1139-1142.
Buettner R, et al. (2002) Activated STAT signaling in human tumors provides novel molecular targets for therapeutic intervention. Clin Cancer Res. 8: 945-954.
Catlett-Falcone R, et al. (1999) STAT proteins as novel targets for cancer therapy. Signal transducer an activator of transcription. Curr Opin Oncol. 11: 490-496.
Coleman DR IV, et al. (2005) Investigation of the binding determinants of phosphopeptides targeted to the SRC homology 2 domain of the signal transducer and activator of transcription 3. Development of a high-affinity peptide inhibitor. J Med Chem. 48: 6661-6670.
Darnell JE. (2005) Validating Stat3 in cancer therapy. Nat Med. 11: 595-596.
Decker T, et al. (1999) Transcription factor activity of Stat proteins: structural requirements and regulation by phosphorylation and interacting proteins. Cell Mol Life Sci. 55: 1535-1546.
Fletcher S, et al. (2008) Molecular approaches towards the inhibition of the signal transducer and activator of transcription 3 (Stat3) protein. ChemMedChem. 3: 1159-1168.
Garcia R, et al. (2001) Constitutive activation of Stat3 by the Src and JAK tyrosine kinases participates in growth regulation of human breast carcinoma cells. Oncogene. 20: 2499-2513.
Gunning PT, et al. (2007) Isoform selective inhibition of STAT1 or STAT3 homo-dimerization via peptidomimetic probes: structural recognition of STAT SH2 domains. Bioorg Med Chem Lett. 17: 1875-1878.
Gunning PT, et al. (2008) Targeting protein-protein interactions: suppression of Stat3 dimerization with rationally designed small-molecule, nonpeptidic SH2 domain binders. Chembiochem. 9: 2800-2803.
Jones G, et al. (1997) Development and validation of a genetic algorithm for flexible docking J Mol Biol. 267: 727-748.
LePecq JB, et al. (1967) A fluorescent complex between ethidium bromide and nucleic acids. Physical-chemical characterization. J Mol Biol. 27: 87-106.
Sartor CI, et al. (1997) Role of epidermal growth factor receptor and STAT-3 activation in autonomous proliferation of SUM-102PT human breast cancer cells. Cancer Res. 57: 978-987.
Schust J, et al. (2004) A high-throughput fluorescence polarization assay for signal transducer and activator of transcription 3. Anal Biochem. 330: 114-118.
Schust J, et al. (2006) Stattic: a small-molecule inhibitor of STAT3 activation and dimerization. Chem Biol. 13: 1235-1242.
Siddiquee K, et al. (2007a) Selective chemical probe inhibitor of Stat3, identified through structure-based virtual screening, induces antitumor activity. Proc Natl Acad Sci USA. 104: 7391-7396.
Siddiquee K, et al. (2007b) An oxazole-based small-molecule Stat3 inhibitor modulates Stat3 stability and processing and induces antitumor cell effects. ACS Chem Biol. 2: 787-798.
Song H, et al. (2005) A low-molecular-weight compound discovered through virtual database screening inhibits Stat3 function in breast cancer cells. Proc Natl Acad Sci USA. 102: 4700-4705.
Toogood, P. (2002) Inhibition of protein-protein association by small molecules: approaches and progress. J Med Chem. 45: 1543-1558.
Turkson J, et al. (2001) Phosphotyrosyl peptides block Stat3-mediated DNA binding activity, gene regulation, and cell transformation. J Biol Chem. 276: 45443-45455.
Turkson J, et al. (2004) Novel peptidomimetic inhibitors of signal transducer and activator of transcription 3 dimerization and biological activity. Mol Cancer Ther. 3: 261-269.
Turkson J. (2004) STAT proteins as novel targets for cancer drug discovery. Expert Opin Ther Targets. 8: 409-422.
Wei LH, et al. (2003) Interleukin-6 promotes cervical tumor growth by VEGF-dependent angiogenesis via a STAT3 pathway. Oncogene. 22: 1517-1527.
International Search Report issued on Nov. 20, 2009 for PCT Application No. PCT/US2009/57291 filed on Sep. 17, 2009, which published as WO 2010/033685 on Mar. 25, 2010 (Applicants—University of Central Florida Research Foundation, et al. // Inventors—James Turkson, et al.) (2 Pages).
Written Opinion issued on Nov. 20, 2009 for PCT Application No. PCT/US2009/57291 filed on Sep. 17, 2009, which published as WO 2010/033685 on Mar. 25, 2010 (Applicants—University of Central Florida Research Foundation, et al. // Inventors—James Turkson, et al.) (6 Pages).
International Preliminary Report on Patentability issued on Mar. 22, 2011 for PCT Application No. PCT/US2009/57291 filed on Sep. 17, 2009, which published as WO 2010/033685 on Mar. 25, 2010 (Applicants—University of Central Florida Research Foundation, et al. // Inventors—James Turkson, et al.) (7 Pages).
Notice of Abandonment issued Apr. 4, 2013 for Canadian Application No. CA 2737360, which claims priority to PCT/US2009/57291 filed on Sep. 17, 2009 (Applicants—University of Central Florida Research Foundation, et al. // Inventors—James Turkson, et al.) (1 Page).
Communication pursuant to Rules 161(2) and 162 EPC issued on May 30, 2011 for European Patent Application No. 09815184.8, which claims priority to PCT/US2009/57291 filed on Sep. 17, 2009 (Applicants—University of Central Florida Research Foundation, et al. // Inventors—James Turkson, et al.) (2 Pages).
Response to Communication pursuant to Rules 161(2) and 162 EPC filed Dec. 6, 2011 for European Patent Application No. 09815184.8, which claims priority to PCT/US2009/57291 filed on Sep. 17, 2009 (Applicants—University of Central Florida Research Foundation, et al. // Inventors—James Turkson, et al.) (11 Pages).
Communication conveying extended European Search Report issued Jan. 25, 2012 for European Patent Application No. 09815184.8, which claims priority to PCT/US2009/57291 filed on Sep. 17, 2009 (Applicants—University of Central Florida Research Foundation, et al. // Inventors—James Turkson, et al.) (5 Pages).
Noting of loss of rights pursuant to Rule 112(1) EPC issued on Oct. 1, 2012 for European Patent Application No. 09815184.8, which claims priority to PCT/US2009/57291 filed on Sep. 17, 2009 (Applicants—University of Central Florida Research Foundation, et al. // Inventors—James Turkson, et al.) (2 Pages).

* cited by examiner

INHIBITORS OF STAT3

RELATED APPLICATION

This application claims priority from U.S. provisional application Ser. No. 61/097,693, which was filed on 17 Sep. 2008, and which is incorporated herein by reference in its entirety.

STATEMENT REGARDING FEDERALLY SPONSORED RESEARCH OR DEVELOPMENT

This invention was made with government support under CA106439 and CA128865 awarded by the National Institutes of Health. The government has certain rights in the invention.

FIELD OF THE INVENTION

The present invention relates to the field of cellular dysfunction diseases such as cancer and, more particularly, to diseases characterized by overexpression of STAT3 protein.

BACKGROUND OF THE INVENTION

STAT3 is the acronym for signal transducer and activator of transcription 3. As the name implies, STAT3 is a transcription factor and, in humans, it is encoded by the gene appropriately known as the STAT3 gene.

STAT3 is a protein which belongs in a family of related STAT proteins. STAT proteins are phosphorylated in response to various growth factors and cytokines which are associated with cell receptors. The phoshorylated STAT proteins then form either homo or heterodimers which move into the cell nucleus to function as transcription activators. Growth factors and cytokines which are known to activate STAT proteins include IL5, IL6, LIF, IFNs, EGF and BMP2.

STAT3 is known to be responsible for mediating expression of many genes when the cell is exposed to stimuli. Accordingly, STAT3 has a central role in important cellular processes involving cell growth and death, apoptosis.

Presence of constitutive STAT3 is found in a number of human cancers and has also been found to be an indicator of poor outcome. Constitutive STAT3 promotes cancerous cell growth by being anti-apoptotic and also stimulating uncontrolled cell proliferation.

Suppression of constitutive STAT3 protein activation in human malignancies represents an important target for molecular therapeutic intervention. STAT proteins mediate the relay of extracellular signals from various cell surface protein receptors to the nucleus, where they help to initiate and regulate specific anti-apoptotic and cell survival gene expression. In part cular, the STAT3 protein isoform is known to directly up-regulate Bcl-XL, c-Myc, Mcl-I, VEGF and cyclin DI/D2, contributing directly to compromised cellular regulation by stimulating cell proliferation and preventing apoptosis in numerous human cancers.

STAT3 activation occurs via phosphorylation of tyrosine 705, which promotes STAT dimerformation through reciprocal STAT phosphotyrosine-SH2 domain interactions." STAT dimers then translocate to the nucleus, where they regulate unique gene expression programs through interaction with specific DNA response elements. STAT3 targeted gene expression confers resistance to apoptosis in many tumor cells. and promotes cell survival, contributing to the resistance of these cancers to currently available chemotherapeutics. Successful STAT3 inhibitors may thus be used to sensitize human cancers with constitutively active STAT3 to existing chemotherapeutic agents, potentially reducing the side effects associated with conventional, aggressive chemotherapy.

Despite the difficulties in identifying protein surface-recognition agents, the promise of STAT3 modulators warrants investigation. Successful peptidic and nonpeptidomimetic small molecules that are capable of targeting malignant cell lines with constitutively activated Stat3 protein are limited to a few examples that include Stattic, STA-21, and S3I-201, which were all identified through high-throughput virtual or biochemical screening approaches. Our first-generation designs were simple peptidomimetics derived from the natural sequence, of which ISS610 was the most potent (see FIG. 1). More recently we have discovered S3I-M2001 (compound 15, Table 1) an oxazole-based small-molecule inhibitor that shows promising inhibition of Stat3 function, and we herein report a family of rationally designed small-molecule, nonpeptidic Stat3 inhibitors.

These agents inhibit Stat3 protein dimerization and induce apoptosis in Stat3-transformed cells and Stat3-dependent breast oncogenic cell lines. The crystal structure of the Stat3-SH2 domain reveals a shallow triangular pocket that is composed of two hydrophobic sites and a hydrophilic phosphate-recognition pocket. Docking studies on our initial lead, peptidomimetic, ISS610, showed that only the hydrophobic pockets in the binding domain were effectively occupied (See FIG. 1 A). To address this problem we theorized that trisubstituted heterocyclic scaffolds, such as oxazoles and thiazoles, might effectively access all three sites (FIG. 1B).

SUMMARY OF THE INVENTION

With the foregoing in mind, the present invention discloses various small molecule compounds which are inhibitors of STAT3. Additionally, the invention includes compositions containing the disclosed STAT3 inhibitory compounds, as well as methods of treatment employing these compounds and compositions.

The present investigation sought to rationally develop small molecule probes derived from the native STAT3 binding sequence. Herein reported is the first rational design and synthesis of small molecule STAT3 inhibitors which selectively inhibit STAT3 protein dimerization and induce apoptosis in STAT3 transformed cells and STAT3-dependent breast and pancreatic oncogenic cell lines.

As noted above, the crystal structure of the STAT3-SH2 domain includes a shallow triangular pocket containing two hydrophobic sites and a hydrophilic phosphate-recognition pocket. Docking studies of the initial lead compound, peptidomimetic ISS610, indicated that only the hydrophobic pockets in the binding domain were effectively occupied (See FIG. 1A). Therefore, it was theorized that perhaps trisubstituted heterocyclic scaffolds, such as oxazoles and thiazoles, might effectively access all three sites (FIG. 1B). Flexible ligand-docking studies (GOLD) directed the design and assembly of oxazole and thiazole scaffolds. The compounds of the present invention were prepared as outlined in the scheme shown in FIG. 2 and below; the thiazole derivatives were synthesized via traditional hantzsch synthetic protocols.

General Procedure A (Alkylation of N-(Diphenylmethylene)glycine ethyl ester): To a flame dried three necked flask under nitrogen and fitted with an over head mechanical stirrer was added N-(Diphenylmethylene)glycine ethyl ester (1 eq) and THF (2 mL/mmol). The resulting solution was cooled to −78° C., and LiHMDS (1.0 M, 1.1 eq) was added. A thick yellow precipitate forms slowly over 4 hours, at which time a solution of the required acid chloride (1.0 eq) in THF (1 mL/mmol) is added dropwise over 1 hour. After complete addition of the acid chloride, the resulting solution was allowed to warm slowly to room temperature over night, and then the reaction was quenched with 2M HCl (1 mL/mmol). The resulting solution was washed twice with EtOAc (1 mL/mmol), and the aqueous layer evaporated to dryness. The resulting solid was dissolved in methanol (0.5 mL/mmol), and an equal amount EtOAc added to induce complete precipitation of inorganic salts, which were then removed by filtration. The resulting solution was reduced to dryness, and the product used without further purification.

General Procedure B (Amide formation from Acids): The required acid (1.0 eq) was added in one portion to a solution of HBTU (1.1 eq) and DIPEA (3.0 eq) in DMF (1 mL/mmol), and the resulting solution stirred at room temperature for 10 minutes. The required amine was then dissolved in a solution of DIPEA (2.0 eq) in DMF (1 mL/mmol) and added to the activated acid in one portion. The resulting solution was stirred for 4 hours, then diluted with EtOAc (10 mL/mmol) and washed successively with equal volumes of: brine, 2M HCl, saturated bicarbonate and brine. The organic layer was dried over magnesium sulfate, and the solvent was removed under reduced pressure to afford the desired amide.

General Procedure C (Oxazole formation): Iodine (1.1 eq) was added to a solution of triphenylphosphine (1.1 eq) dissolved in DCM (20 mL/mmol) in a flame dried flask under nitrogen, and the resulting yellow solution stirred for 5 minutes. TEA (2.2 eq) was then added and the solution stirred under nitrogen for a further 5 minutes. The required amide (1.0 eq) was dissolved in DCM (10 mL/mmol) and added dropwise over 10 minutes to the solution of triphenylphosphine diiodide. After stirring for 4 hours excess tirphenylphosphine diiodide was quenched by addition of MeOH (5.0 eq), and the resulting solution absorbed directly onto silica gel, and purified by FCC.

General Procedure D (Base Ester Hydrolysis): An aqueous solution of sodium hydroxide (2M, 3 eq) was added to a solution of the required ester (1 eq) dissolved in 1:1 THF/Water (40 mL/mmol). The resulting solution was stirred at room temperature over night, and the pH raised to ~7 by addition of 2M HCl. The reaction was extracted into EtOAc (100 mL/mmol), and washed with brine (20 mL/mmol). The organic phase was dried over magnesium sulfate, and solvent removed under reduced pressure to afford the desired carboxylic acid.

General Procedure E (tert-butylation of carboxylic acid). The suitable carboxylic acid (1 equiv) was dissolved in CH2Cl2 (10 ml/mmol), to which tert-Butyl 3,3,3-trichloroacetamide (2 equiv) was added in a solution of cyclohexane (2 ml/mmol) followed by the addition of BF3.etherate (20 μl/mmol). The reaction solution was then stirred at room temperature under an N2 atmosphere for 2 hrs. The reaction was monitored by TLC, until all the starting material had been consumed.

General Procedure F (Hydrogenolysis of benzyl ether): The required benzyl protected phenol (1 equiv) was dissolved in a stirred solution of MeOH:EtOAc (1:1). The solution was then degassed thoroughly before the addition of Pd/C 10% (10 mg/mmol). H2 gas was then bubbled through the solution for 5 mins before the solution was put under an atmosphere of H2 gas and stirred continuously for 3 hrs. The hydrogen gas was excluded from the reaction vessel and the reaction mixture filtered to remove the Pd/C through glass fibre paper. The solution was then concentrated to give pure product.

General Procedure G (Phosphorylation with Phosphoramidate): The required phenol (1 equiv) was dissolved in DMF (1 mL/mmol), 3% w/w tetratrazole in acetonitrile (4 eq), and di-tert-butyl diisopropylphosphoramidate (1.5 eq) was added in one portion. The resulting solution was stirred at room temperature over night, then cooled in an ice bath and then m-CPBA (1.1 eq) was added in small portions. The resulting solution was extracted into EtOAc (20 mL/mmol), and washed successively with 1M HCl, saturated sodium bicarbonate, and brine. The organic phase was dried over magnesium sulfate, and the solvent was removed under reduced pressure.

General Procedure H (tButyl ester TFA mediated deprotection): To a stirred solution of tert-butyl ester (1 eq) in CH2Cl2 (1 mL/mmol) under N2 was added dropwise trifluoroacetic acid (100 equiv) and allowed to stir at room temperature for 3 hrs. The reaction was monitored via TLC and stopped upon consumption of starting material. The solution was concentrated and purified via silica gel chromatography to yield pure carboxylic acid.

General Procedure I involved the hydrogenolysis of benzyl protected phosphate esters, illustrated in the synthetic scheme shown in FIG. 2, as would be known by those skilled in the art.

Synthesis of Oxazole R1=Phenyl Derivatives.

Phosphoric acid mono-[4-(4-hexylcarbamoyl-2-phenyl-oxazol-5-ylmethyl}-phenyl]ester (PGB2-107) (12aa, R1=phenyl, R2=hexyl); Reaction of 11aa according to procedure I, yield after rpHPLC (78%). 1H NMR (MeOD)™ 0.83 (3H, t, J=6.7 Hz, CH3), 1.25-1.34 (8H, m, CH2), 1.50-1.60 (2H, m, CH2), 3.30 (2H, t, J=7.3 Hz, CH2), 4.37 (2H, s, CH2), 7.06 (2H, d, J=8.4 Hz, Ar—H), 7.23 (2H, d, J=8.4 Hz, Ar—H), 7.39 (4H, dd, J=5.1 and 1.8 Hz, Ar—H), 7.90 (1H, m, Ar—H); 13C NMR (MeOD)™ 14.7, 24.0, 28.1, 31.1, 32.2, 33.1, 40.5, 116.2, 122.1, 127.8, 129.1, 130.4, 130.6, 130.9, 137.0, 137.9, 151.2, 154.7, 168.2; HRMS (TOF MS-ES), calcd. for C23H28N2O6P [M+H] m/z=459.1667, fnd. 459.1658; rpHPLC tR: condition (I) 17.106 (II) 15.995 minutes, purity 95%.

Phosphoric acid mono-{4-[4-(3-methoxy-phenylcarbamoyl-2-phenyl-oxazol-5-ylmethyl]-phenyl}ester (PGB2-099) (12ab, R1=phenyl, R2=3-methoxy-aniline); Reaction of 11ab according to procedure I, yield after rpHPLC (89%). 1H NMR (MeOD)™ 3.80 (3H, s, CH3), 6.68-6.72 (1H, m, Ar—H), 7.14 (2H, d, J=8.3 Hz, Ar—H), 7.24 (2H, d, J=5.1 Hz, Ar—H), 7.35 (2H, d, J=8.3 Hz, Ar—H), 7.42-7.50 (4H, m, Ar—H), 8.02 (2H, dd, J=7.4 and 3.4 Hz, Ar—H); 13C NMR (MeOD)™ 29.2, 59.2, 101.0, 111.5, 113.4, 119.4, 119.5, 122.2, 125.3, 125.32, 125.32, 128.1, 128.2, 128.23, 130.1, 130.2, 135.4, 135.42, 138.4, 139.1, 139.5, 140.1, 152.1, 156.7, 163.1, 164.0; HRMS (TOF MS-ES), calcd. for C24H22N2O7P [M+H] m/z=481.1158, fnd. 481.1165; rpHPLC tR: condition (I) 12.287 minutes, purity 99%.

Phosphoric acid mono-{4-[4-(4-cyclohexyl-phenylcarbamoyl)-2-phenyl-oxazol-5-ylmethyl]-phenyl}ester (PGB2-105) (12ac, R1=phenyl, R2=4-cyclohexyl-aniline); Reaction of 11ac according to procedure I, yield after rpHPLC (84%). 1H NMR (MeOD)™ 1.85-2.50 (10H, m, CH2), 3.17 (1H, m, CH), 5.13 (2H, s, CH2), 7.78 (2H, d, J=8.4 Hz, Ar—H), 7.85 (2H, d, J=8.4 Hz, Ar—H), 8.14 (3H, m, Ar—H), 8.25 (2H, d, J=8.5 Hz, Ar—H), 8.65 (2H, dd, J=5.8 and 1.9 Hz, Ar—H); 13C NMR (MeOD)™ 27.2, 28.0, 32.0, 35.7, 45.5, 121.7, 121.78, 122.0, 127.5, 127.8, 128.2, 130.1, 131.0, 131.0, 131.7, 132.2, 134.5, 136.7, 145.9, 156.8, 160.8, 161.7; HRMS (TOF MS-ES), calcd. for C29H30N2O6P [M+H] m/z=533.1849, fnd. 533.1842; rpHPLC tR: condition (I) 16.137 (III) 16.480 minutes, purity 99%.

Phosphoric acid mono-{4-[4-(4-bromo-phenylcarbamoyl)-2-phenyl-oxazol-5-ylmethyl]-phenyl}ester (PGB2-097) (12ad, R1=phenyl, R2=4-bromo-aniline); Reaction of 11ad according to procedure I, yield after rpHPLC (79%). 1H NMR (MeOD)™ 4.52 (2H, s, CH2), 7.14-7.20 (3H, m, Ar—H), 7.18 (2H, d, J=8.5 Hz, Ar—H), 7.38 (4H, dd, J=13.5 and 6.0 Hz, Ar—H), 7.48-7.52 (2H, m, Ar—H), 7.88 (2H, d, J=7.8 Hz, Ar—H), 8.04 (2H, d, J=7.8 and 4.0 Hz, Ar—H); 13C NMR (MeOD)™ 32.0, 121.7, 121.9, 125.7, 127.6, 127.8, 129.9, 130.1, 131.0, 131.7, 132.2, 134.4, 139.1, 152.1, 157.0, 160.8, 161.8; HRMS; rpHPLC tR: condition (I) 10.970 (II) 8.266 minutes, purity 99%.

Phosphoric acid mono-{4-[4-(3-bromo-phenylcarbamoyl)-2-phenyl-oxazol-5-ylmethyl]-phenyl}ester (PGB2-139) (12ae, R1=phenyl, R2=3-bromo-aniline); Reaction of 11ae according to procedure I, yield after rpHPLC (83%). 1H NMR (MeOD)™ 4.50 (2H, s, CH2), 7.15 (1H, d, J=7.4 Hz, Ar—H), 7.18 (2H, d, J=8.5 Hz, Ar—H), 7.34 (2H, d, J=8.5 Hz, Ar—H), 7.38 (1H, t, J=8.5 Hz, Ar—H), 7.51 (3H, m, Ar—H), 7.74 (2H, d, J=8.6 Hz, Ar—H), 8.05 (2H, dd, J=5.4 and 1.8 Hz, Ar—H); 13C NMR (MeOD)™ 32.4, 115.9, 118.7, 122.2, 122.24, 122.3, 125.0, 126.0, 127.9, 130.3, 130.4, 131.0, 132.5, 136.9, 137.5, 137.9, 149.8, 157.7, 150.9, 165.7; rpHPLC tR: condition (I) 15.682 (II) 14.019 minutes, purity 98%.

Synthesis of Oxazole R1=Naphthyl Derivatives.

Phosphoric acid mono-[4-(4-hexylcarbamoyl-2-naphthalen-1-yl-oxazol-5-ylmethyl)-phenyl]ester (PGB2-227) (12ca, where R1=naphthyl, R2=hexyl); Reaction of 11ca according to procedure I, yield after rpHPLC (74%). 1H NMR (MeOD)™ 0.89 (3H, t, J=6.9 Hz, CH3), 1.23-1.44 (6H, m, CH2), 1.59-1.68 (2H, m, CH2), 3.39 (2H, t, J=7.3 Hz, CH2), 4.50 (2H, s, CH2), 7.13 (2H, d, J=8.5 Hz, Ar—H), 7.37 (2H, d, J=8.5 Hz, Ar—H), 7.50-7.64 (3H, m, Ar—H), 7.90 (1H, d, J=8.1 Hz, Ar—H), 7.99 (1H, d, J=8.1 Hz, Ar—H), 8.09 (1H, d, J=7.3 Hz, Ar—H), 9.13 (1H, d, J=8.6 Hz, NH); 13C NMR (MeOD)™ 14.7, 24.1, 28.2, 31.1, 32.3, 33.1, 41.6, 116.3 (2×C), 122.1, 125.2, 125.9, 126.5, 127.9 (2×C), 129.1, 129.6, 130.1, 131.3 (3×C), 133.9, 134.9, 135.8, 151.4, 156.2, 160.3; HRMS (TOF MS-ES+), calcd. for C27H30NO6P [M+H] m/z=509.1856, fnd. 509.1842; rpHPLC tR: condition (I) 13.489 (II) 12.213 minutes, purity 100%.

Phosphoric acid mono-{4-[4-(3-methoxy-phenylcarbamoyl)-2-naphthalen-1-yl-oxazol-5-ylmethyl]-phenyl}ester (PGB4-091); Reaction of 11cb according to procedure I, yield after rpHPLC (45%). 1H NMR (MeOD)™ 3.85 (3H, s, CH3), 4.61 (2H, s, CH2), 6.76 (1H, td, J=6.4 and 2.5 Hz, Ar—H), 7.21 (2H, d, J=8.4 Hz, Ar—H), 7.29-7.32 (2H, m, Ar—H), 7.45 (2H, d, J=8.4 Hz, Ar—H), 7.50-7.53 (1H, m, Ar—H), 7.59 (2H, dd, J=8.1 and 7.3 Hz, Ar—H), 7.69 (1H, ddd, J=8.5, 6.8 and 1.3 Hz, Ar—H), 7.97 (1H, d, J=7.8 Hz, Ar—H), 8.06 (1H, d, J=8.2 Hz, Ar—H), 8.17 (1H, dd, J=7.3 and 1.0 Hz, Ar—H), 9.12 (1H, dd, J=8.6 Hz, Ar—H); 13C NMR (MeOD)™ 32.4, 56.1, 108.1, 111.8, 114.6, 122.1, 124.5, 126.4, 127.2, 127.9, 129.2, 129.8, 130.1, 131.0, 131.4, 131.6, 132.0, 133.3, 134.7, 135.8, 140.6, 152.4, 157.3, 161.0, 162.0, 162.3; HRMS (TOF MS-ES+), calcd. for C28H24NO7P [M+H] m/z=531.1331, fnd. 531.1321; rpHPLC tR: condition (I) 13.064 (II) 11.925 minutes, purity 100%.

Phosphoric acid mono-{4-[4-(4-cyclohexyl-phenylcarbamoyl)-2-naphthalen-1-yl-oxazol-5-ylmethyl]-phenyl}ester (PGB2-067); Reaction of 11cc according to procedure I, yield after rpHPLC (79%). 1H NMR (DMSO) 1.20-1.41 (5H, m, CH2), 1.65-1.82 (5H, m, CH2), 2.49, (1H, tt, J=10.1 and 2.6 Hz, Ar—H), 4.51 (2H, s, CH2), 7.11 (2H, d, J=7.9 Hz, Ar—H), 7.21 (2H, d, J=8.3 Hz, Ar—H), 7.31 (2H, d, J=7.9 Hz, Ar—H), 7.64 (2H, dd, J=14.3 and 7.1 Hz, Ar—H), 7.70 (1H, dd, J=8.1 and 7.2 Hz, Ar—H), 7.74 (2H, d, J=8.4 Hz, Ar—H), 8.03 (1H, d, J=8.4 Hz, Ar—H), 8.13 (1H, d, J=8.1 Hz, Ar—H), 8.18 (1H, d, J=7.2 Hz, Ar—H), 9.24 (1H, d, J=8.4 Hz, Ar—H), 10.04 (1H, s, NH); 13C NMR (DMSO)™ 25.6, 26.4, 30.5, 34.0, 43.3, 120.3, 121.1, 122.3, 125.2, 126.0, 126.6, 126.63, 127.9, 128.2, 129.2, 129.4, 130.5, 131.8, 133.5, 135.9, 143.4, 155.1, 158.1, 159.6; HRMS (TOF MS-ES+), calcd. for C27H30NO6P [M+H] m/z=509.1856, fnd. 509.1842; rpHPLC tR: condition (I) 15.019 (II) 14.914 minutes, purity 93%.

Synthesis of Thiazole R1=Phenyl Derivatives

Phosphoric acid mono-[4-(4-hexylcarbamoyl-2-phenyl-thiazol-5-ylmethyl)-phenyl]ester (PGB3-139) (23aa, R1=phenyl, R2=hexyl); Reaction of 22aa according to procedure F, yield after rpHPLC (85%). 1H NMR (MeOD)™ 0.86 (3H, t, J=6.7 Hz, CH3), 1.25-1.39 (6H, m, CH2), 1.59 (2H, m, CH2), 3.34 (2H, t, J=7.2 Hz, CH2), 4.62 (2H, s, CH2), 7.10 (2H, d, J=8.2 Hz, Ar—H), 7.27 (2H, d, J=8.0 Hz, Ar—H), 7.36-7.39 (3H, m, Ar—H), 7.87 (2H, dd, J=6.0 and 2.4 Hz, Ar—H); 13C NMR (MeOD)™ 14.4, 23.7, 27.8, 30.7, 32.7, 32.9, 40.3, 121.7, 127.4, 130.1, 130.9, 131.6, 134.2, 137.7, 144.5, 146.8, 152.3, 164.5, 165.9; HRMS (TOF MS-ES), calcd. for C24H22N2O6PS [M+H] m/z=497.0936, fnd. 497.0958; rpHPLC tR: condition (I) 12.518 (II) 11.103 minutes, purity 100%.

Phosphoric acid mono-{4-[4-(3-methoxy-phenylcarbamoyl)-2-phenyl-thiazol-5-ylmethyl]-phenyl}ester (PGB3-143) (23ab, R1=phenyl, R2=3-methoxy aniline); Reaction of 22ab according to procedure F, yield after rpHPLC (82%). 1H NMR (MeOD)™ 3.80 (2H, s, CH3), 4.69 (2H, s, CH2), 6.71 (1H, dt, J=6.5 and 2.5 Hz, Ar—H), 7.16 (2H, d, J=8.5 Hz, Ar—H), 7.23-7.27 (2H, m, Ar—H), 7.32 (2H, d, J=8.2 Hz, Ar—H), 7.43-7.48 (4H, m, Ar—H), 7.95-7.98 (2H, m, Ar—H); HRMS (TOF MS-ES+), calcd. for C24H22N2O6SP [M+H] m/z=497.0936, fnd. 497.0958; rpHPLC tR: condition (I) 12.667 minutes, purity 99%.

Phosphoric acid mono-{4-[4-(4-cyclohexyl-phenylcarbamoyl)-2-phenyl-thiazol-5-ylmethyl]-phenyl}ester (PGB3-147) (23ac, R1=phenyl, R2=4-cyclohexyl phenyl); Reaction of 22ac according to procedure F, yield after FCC (67%, 33% ethyl acetate in hexanes). 1H NMR (DMSO)™ 1.19-1.42 (6H, m, CH2), 1.69 (1H, d, J=13.5 Hz, CH2), 1.78 (2H, d, J=8.3 Hz, CH2), 2.52 (1H, m, CH), 4.65 (2H, s, CH2), 7.11 (2H, s (broad), Ar—H), 7.21 (2H, d, J=7.4 Hz, Ar—H), 7.29 (2H, s (broad), Ar—H), 7.49 (2H, s (broad), Ar—H), 7.74 (2H, d, J=7.4 Hz, Ar—H), 7.95 (1H, t, J=6.1 Hz, Ar—H), 8.05 (2H, m, Ar—H), 10.15 (1H, s, NH); HRMS (TOF MS-ES+), calcd. for C26H24NO4 [M+H] m/z=475.1465, fnd. 475.1457; rpHPLC tR: condition (I) 16.033, purity 100%.

Synthesis of Thiazole R1=Napthyl Derivatives

Phosphoric acid mono-[4-(4-hexylcarbamoyl-2-naphthalen-1-yl-thiazol-5-ylmethyl]-phenyl}ester (PGB3-291) (23bb, R1=naphthyl, R2=4-methoxy phenyl) (PGB3-291) (23ba, R1=naphthyl, R2=hexyl aniline); 1H NMR (CDCl3) 0.83 (3H, t, J=6.5 Hz, CH3), 1.24-1.38 (6H, m, CH2), 1.50-1.51 (2H, m, CH2), 3.36-3.39 (2H, m, CH2), 4.57 (2H, s, CH2), 7.04-7.20 (3H, m, Ar—H), 7.38-7.60 (4H, m, Ar—H), 7.75 (1H, s, Ar—H), 7.84 (2H, t, J=8.3 Hz, Ar—H), 8.55 (1H, d, J=7.6 Hz, Ar—H); 13C NMR (CDCl3) 13.9, 22.5, 26.5, 29.3, 31.4, 32.0, 39.7, 120.9, 125.0, 125.3, 126.4, 127.3, 128.4, 128.7, 129.7, 130.2, 130.7, 133.9, 146.5, 149.5, 155.01, 163.7; HRMS (TOF MS-ES+), calcd. for C27H30N2O5PS [M+H] m/z=525.1596, fnd. 525.1579; rpHPLC tR: condition (I) 15.908, (II) 16.140 minutes, purity 99%.

Phosphoric acid mono-{4-[4-(3-methoxy-phenylcarbamoyl)-2-naphthalen-1-yl-thiazol-5-ylmethyl]-phenyl}ester (PGB4-003) (23bb, R1=naphthyl, R2=4-methoxy phenyl); 1H NMR (CDCl3) 3.67 (3H, s, CH3), 4.50 (2H, s, CH2), 6.57 (1H, d, J=8.0 Hz, Ar—H), 6.96-7.46 (11H, m, Ar—H), 7.68-

7.78 (2H, m, Ar—H), 8.50 (1H, d, J=6.7 Hz, Ar—H), 9.34 (1H, s, NH); 13C NMR (CDCl3) 33.1, 56.0, 106.1, 110.9, 112.8, 125.6, 125.8, 127.1, 128.1, 129.1, 129.3, 130.3, 130.35, 130.5, 130.6, 131.5, 134.6, 137.9, 139.5, 150.4, 153.9, 161.8, 165.0; HRMS (TOF MS-ES+), calcd. for C28H24N2O6PS [M+H] m/z=547.1091, fnd. 547.1093; rpHPLC tR: condition (I) 14.935, (II) 15.048 minutes, purity 97%.

Phosphoric acid mono-{4-[4-(4-cyclohexyl-phenylcarbamoyl)-2-naphthalen-1-yl-thiazol-5-ylmethyl]-phenyl}ester (PGB4-289) (23bc, R1=naphthyl, R2=4-cyclohexyl aniline); 1H NMR (CDCl3) 1.22-1.39 (5H, m, CH2), 1.67 (1H, d, J=12.0 Hz, CH), 1.70-1.81 (4H, m, CH2), 2.41 (1H, t, J=11.6 Hz, CH), 4.59 (2H, s, CH2), 6.95-7.17 (6H, m, Ar—H), 7.38 (1H, t, J=7.5 Hz, Ar—H), 7.42-7.49 (4H, m, Ar—H), 7.54 (1H, d, J=7.0 Hz, Ar—H), 7.81 (2H, t, J=6.4 Hz, Ar—H), 8.56 (1H, d, J=8.2 Hz, Ar—H); 13C NMR (CDCl3) 26.5, 27.2, 32.7, 34.8, 44.4, 120.9, 121.3, 125.4, 125.7, 126.8, 127.7, 127.8, 128.8, 129.2, 130.3, 130.5, 131.2, 134.3, 135.2, 136.5, 142.8, 145.0, 148.0, 149.8, 161.0, 164.1; HRMS (TOF MS-ES+), calcd. for C27H30N2O5PS [M+H] m/z=525.1596, fnd. 525.1613; rpHPLC tR: condition (I) 13.898, (II) 13.025 minutes, purity 99%.

Trifluoro-methanesulfonic acid 4-[4-(4-cyclohexyl-phenylcarbamoyl)-2-phenyl-oxazol-5-ylmethyl]-phenyl ester (PGB3-203) (XX, R1=phenyl, R2=4-cyclohexyl aniline); 1H NMR (CDCl3)™ 1.23-1.45 (4H, m, CH2), 1.68-2.93 (6H, m, CH2), 2.50 (1H, t, J=11.5 and 3.0 Hz, CH), 4.58 (2H, s, CH2), 7.21 (2H, d, J=8.4 Hz, Ar—H), 7.23 (2H, d, J=8.4 Hz, Ar—H), 7.46-7.53 (4H, m, Ar—H), 7.61 (2H, d, J=8.4 Hz, Ar—H), 8.02 (2H, dd, J=6.55 and 3.1 Hz, Ar—H), 8.86 (1H, s, NH); 13C NMR (CDCl3)™ 26.0, 26.8, 31.32, 34.5, 43.9, 120.0, 121.5, 126.4, 126.5, 127.3, 128.9, 130.7, 131.2, 135.1, 137.3, 144.6, 148.7, 153.9, 159.5; LRMS (MS-ES+), m/z=585.1 [M+H]; rpHPLC tR: condition (I) 16.360, (II) 16.375 minutes, purity 99%.

2-{4-[4-(4-Cyclohexyl-phenylcarbamoyl)-2-phenyl-oxazol-5-ylmethyl]-phenoxy}-malonic acid (PGB3-213) (XX, R1=phenyl, R2=4-cyclohexyl aniline); 1H NMR (CDCl3)™ 1.20-1.48 (5H, m, CH2), 1.68-1.86 (5H, m, CH2), 2.46 (1H, t, J=8.4 Hz, CH), 4.43 (2H, s, CH2), 5.15 (1H, s, CH), 6.91 (2H, d, J=7.3 Hz, Ar—H), 7.18 (2H, d, J=8.4 Hz, Ar—H), 7.29 (2H, d, J=7.3 Hz, Ar—H), 7.44-7.47 (3H, m, Ar—H), 7.57 (2H, d, J=8.4 Hz, Ar—H), 7.99 (2H, t, J=3.7 Hz, Ar—H), 9.60 (1H, s, NH); 13C NMR (CDCl3) 227.3, 28.0, 31.9, 35.8, 45.5, 96.3, 116.6, 122.0, 127.5127.8, 128.2, 130.1, 131.0, 131.5, 131.7, 132.1, 136.7, 145.9, 157.1, 160.7, 161.8; rpHPLC tR: condition (I) 14.347, (II) 13.821 minutes, purity 95%.

Accordingly, a first embodiment of the invention is a compound having a generic chemical structure according to the following formula:

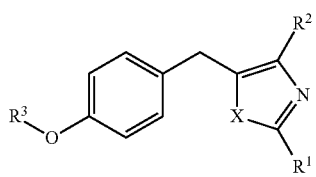

wherein X comprises oxygen or sulfur, $R^1$ comprises a phenyl or naphthyl group, $R^2$ comprises an amide group and $R^3$ comprises a phosphate group. This embodiment of the invention is a generic molecule which forms the basic structure from which the various other embodiments are derived. This and other embodiments of the invention are shown in Table I. These compounds may be prepared according to the scheme shown in FIG. 2. QQ Another compound of the invention is one having a chemical structure according to the formula:

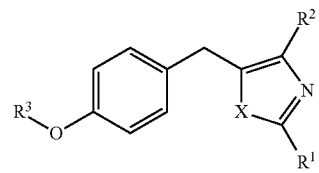

wherein X is oxygen, $R^1$ is a phenyl group, $R^2$ is a naphthyl amide group and $R^3$ is a phosphate group.

Yet another compound of the invention has a chemical structure according to the formula:

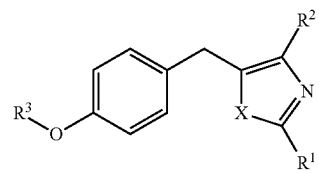

wherein X is sulfur, $R^1$ is a phenyl group, $R^2$ is

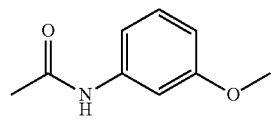

and $R^3$ is a phosphate group.

Another derivative of the present invention includes a compound having a chemical structure according to the formula:

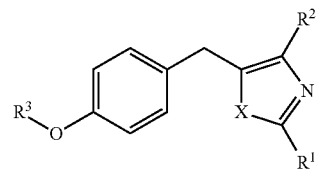

wherein X is oxygen, $R^1$ is a phenyl group, $R^2$ is

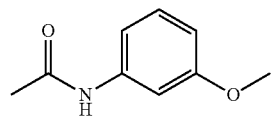

and $R^3$ is a phosphate group.

Yet an additional compound included in the invention is one having a chemical structure according to the formula:

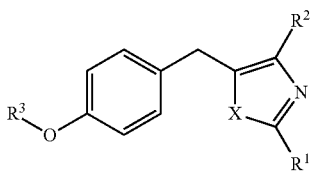

wherein X is sulfur, R¹ is a naphthyl group, R² is

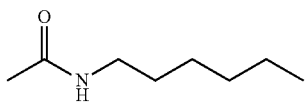

and R³ is a phosphate group.

Another embodiment of the invention includes a compound having a chemical structure according to the formula:

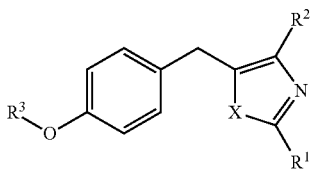

wherein X is oxygen, R¹ is a naphthyl group, R² is

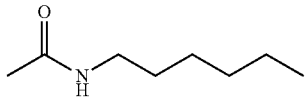

and R³ is a phosphate group.

A further embodiment of the invention is a compound having a chemical structure according to the formula:

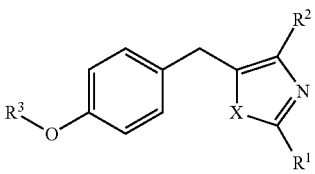

wherein X is sulfur, R¹ is a naphthyl group, R² is

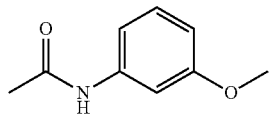

and R³ is a phosphate group.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Aspects of the presently disclosed invention were published by P. T. Gunning et al., Targeting Protein-Protein Interactions: Suppression of STAT3 Dimerization with Rationally Designed Small-Molecule, Nonpeptidic SH2 Domain Binders, *ChemBioChem* 2008, 9, 2800-2803. As noted above, this publication is incorporated herein by reference in its entirety.

The crystal structure of the STAT3-SH2 domain reveals a shallow triangular pocket comprising two hydrophobic sites and a hydrophilic phosphate recognition pocket. Initial peptidomimetic studies failed to identify agents which simultaneously projected functionality within all three pockets; see FIG. 1A.

The present investigation was directed to ascertaining whether a trisubstituted heterocyclic scaffold could effectively access these three pockets; see FIG. 1B. Flexible ligand-docking studies (GOLD) directed the design and assembly of oxazole and thiazole scaffolds. A series of oxazole inhibitors was prepared as outlined in FIG. 2. GOLD docking studies predicted a focused set of diversity elements deemed suitable for occupation of the SH2 domain. Both R' and $R^2$ appendages were predominantly hydrophobic in nature to interact with the hydrophobic surface presented by residues present in the upper (Phe716, Met660, Pro715) and lower right (Ser636, Arg595, Lys591) pockets of the STAT3 active site (FIGS. 1A and B).

Figure 1:
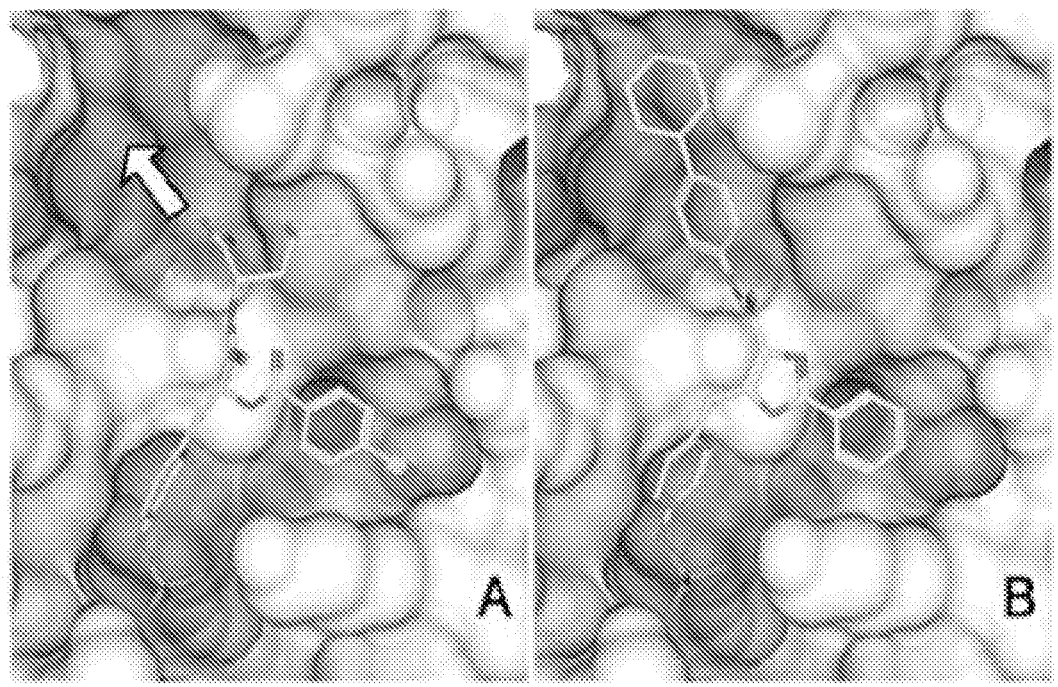
FIG. 1A, according to an embodiment of the present invention, shows the active site conformation of ISS610, as determined by flexible ligand docking in the active site of STAT3 (PDB ID: 1BG1) using GOLD 3.0; lead peptidomimetic ISS610 displays limited occupation of the active site; expansion site indicated by arrow.
FIG. 1B shows how oxazole 10 replicates the functionality projection of ISS610 and accesses the previously unoccupied region of the SH2 domain (red=hydrophobic, blue=hydrophilic)
Figure 1:
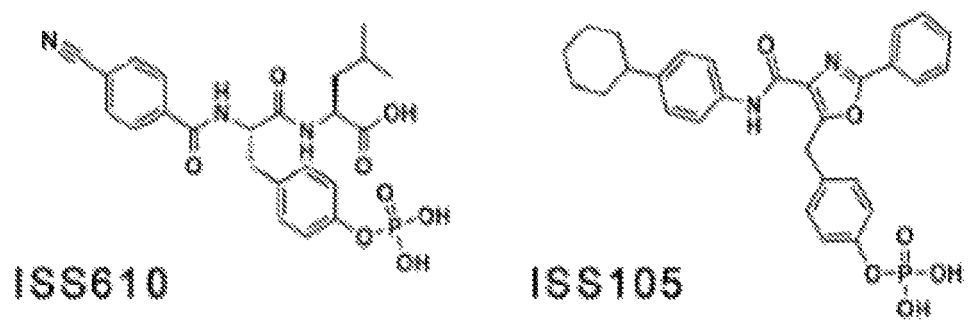
Figure 2:
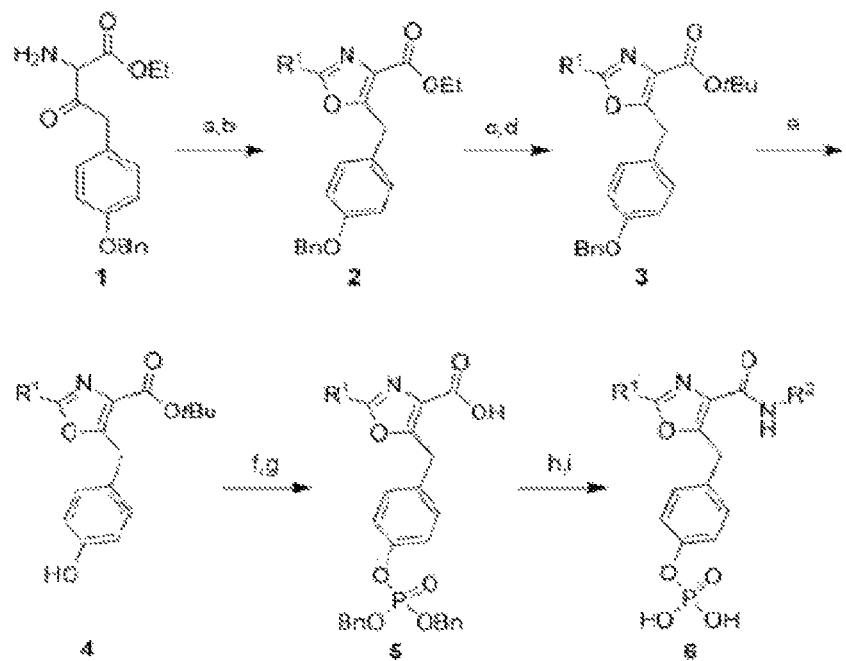
FIG. 2 depicts a reaction scheme including the following conditions: a) R'COOH, HBTU, DIPEA, DMF; b) PPh$_3$, I$_2$, TEA. CH$_2$Cl$_2$; c) 2N NaOH, THF; d) tBu-trichloro acetamide, BF$_3$(OEt)$_2$; CH$_2$Cl$_2$; e) H$_2$, Pd/C, THF; f) dibenzyldiisopropyl phosphoroamidate, tetrazole, mCPBA, CH$_2$Cl$_2$: g) TFA, Et$_5$SiH, CH$_2$Cl$_2$; h) R²COOH, HBTU, DIPEA, DMF; i) H$_2$, Pd/C, EtOAc, HBTU=2-(1H-benzotriazol-1-yl)-1,1,3,3-tetra methyluronium hexafluorophosphate (DIPEA=diisopropylethylamine, DMF=N,N dimethylformamide, TEA=triethylamine, TFA=trifluoroacetic acid).
Figure 3:
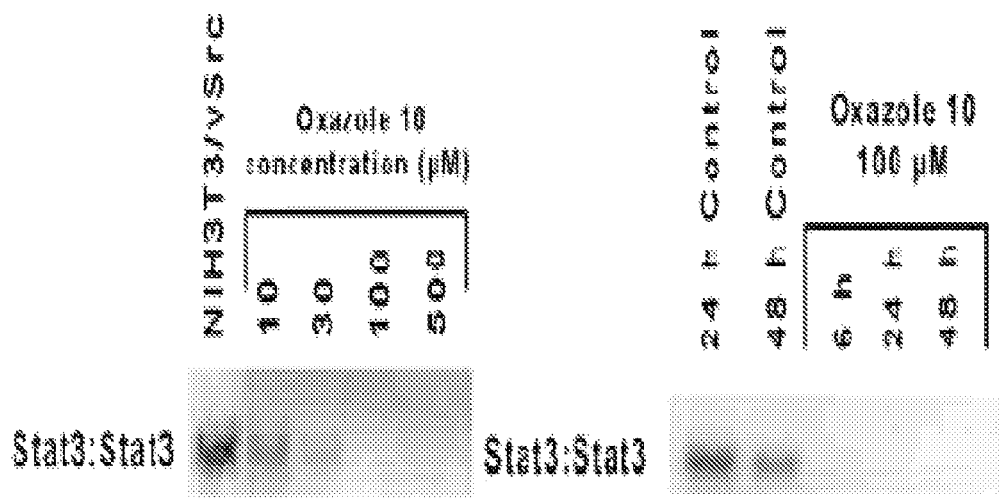
FIG. 3 shows EMSA data. On the left is EMSA data for in vitro disruption of STAT23 dimers by compound 10, as shown in Table 1; On the right is in vivo disruption of NIHJT3/vSrc with compound 10 (100 μM) over 6, 24 and 48 hour periods.
Figure 4:
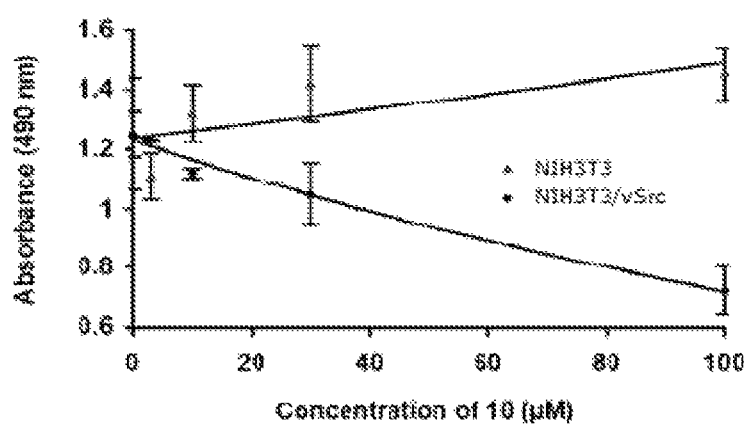
FIG. 4 shows a line graph illustrating the dose dependent effects of compound 10 upon NIH3T3, a mouse breast tissue cell line, and NIH3T3/vSrc cell lines using WST-1 mediated spectrophotometric analysis.
Figure 5:
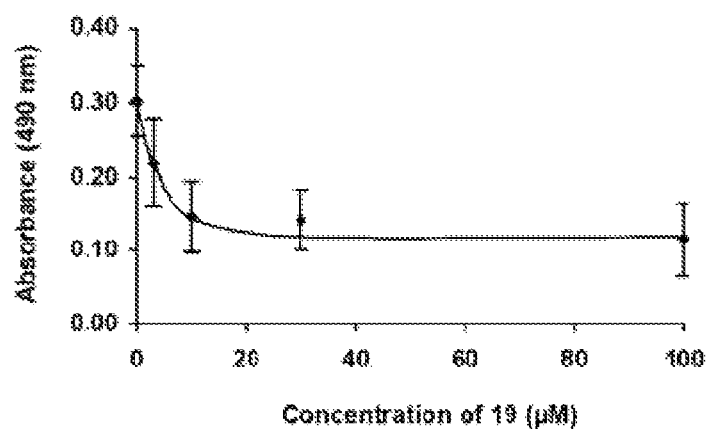
FIG. 5 depicts an EC$_{50}$ determination for compound 19 induced effects upon pancreatic human cancer cell lines (panc-1) evaluated using WST-1.

A screening process evaluated in vitro disruption of STAT3 (dimer)-DNA formation through a previously published EMSA based assays, giving a valuable insight into the inhibitor's mode of action against the STAT3 homo-dimer. An initial series of STAT3 oxazole and thiazole inhibitors is shown in Table 1. Oxazole 7 was prepared as a control agent, closely resembling lead peptidomimetic ISS610, to explore the efficacy of compounds not projecting sizable appendages from the $R^2$ position. STAT3 DNA binding disruption by compound 7 was shown to be negligible, presumably due to poor inhibitor-protein complementarity. Substitution of ISS610 at the acidic terminus had been shown previously to decrease potency in all cases studied, suggesting that the oxazole scaffold is able to project substituents in a substantially different orientation than could be achieved with a peptide based inhibitor (FIG. 1).

Five compounds shown in Table 1 displayed $IC_{50}$ values below 100 μM, with oxazole 10 showing significant dimer disruption potential ($IC_{50}$=33 μM). Data suggest limited isoform specificity for STAT3 over STAT1 protein.

Dramatic effects were observed though replacement of the central core in several cases. Examples of such effects include compounds 10 and 11 as shown in Table 1, where the high potency displayed by the oxazole analog 10 $IC_{50}$=33 μM (see FIG. 2A.) is severely diminished in the analogous thiazole 11 ($IC_{50}$=775 μM). Conversely, thiazole 16 ($IC_{50}$=25 μM) exhibits improvements in activity compared with the corresponding oxazole 15 ($IC_{50}$=58 μM). Molecular modeling studies showed that the thiazole scaffolds afforded a functional group orientation with higher protein surface complementarity.

Docking studies predict a H-bond between Lys591 and the heterocyclic core oxygen or sulfur, which is expected to be more favorable with harder oxazole oxygen atoms than softer thiazole sulfur. In almost all examples, increased potency is derived from a thiazole core.

Control oxazole compound 12, containing the most potent arrangement of $R^1$ and $R^2$ elements, but lacking a phosphate group, was shown to be essentially devoid of activity. Further non-phosphorylated scaffolds were prepared and found to be impotent STAT3 disruptors.

Given the extended planar aryl-oxazole construct and the propensity of such scaffolds to intercalate with DNA, experiments were conducted to discount potential DNA interaction. It was found using fluorescence spectroscopy that DNA-bound ethidium bromide did not vary upon addition of compound 10, which can thus be considered inert towards DNA.

Work was undertaken to establish the affinity of the lead oxazole 10 for the inactive (unphosphorylated) STAT3 monomer to help determine the mode of action. By using fluorescence spectroscopy, $K_i$ values were calculated through displacement of an SH2 binding fluorescein-labeled GpYLPQTV-NH2 peptide. The most potent inhibitors were found to have low affinity with the

TABLE 1

$IC_{50}$ values (μM) for the inhibition of STAT3 DNA-binding activity in vitro via oxazole and thiazole analogs of ISS610.

| Compound Number | $R^1$ | $R^2$ | Scaffold Core | $R^3$ | $IC_{50}$ Values (μM)[a] |
|---|---|---|---|---|---|
| 7 | phenyl | C(=O)OH | oxazole | $PO_3H_2$ | >1000 |
| 8 | phenyl | C(=O)NH-pentyl | oxazole | $PO_3H_2$ | >1000 |

TABLE 1-continued
IC$_{50}$ values (μM) for the inhibition of STAT3 DNA-binding activity in vitro via oxazole and thiazole analogs of ISS610.
| Compound Number | R$^1$ | R$^2$ | Scaffold Core | R$^3$ | IC$_{50}$ Values (μM)[a] |
|---|---|---|---|---|---|
| 9 | 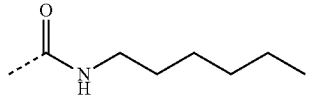 |  |  | PO$_3$H$_2$ | 150 |
| 10 | 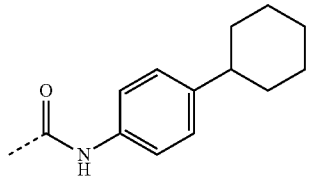 |  |  | PO$_3$H$_2$ | 33 |
| 11 | 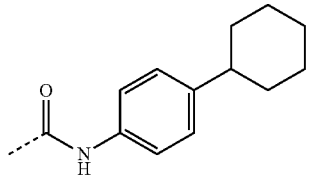 |  |  | PO$_3$H$_2$ | 775 |
| 12 | 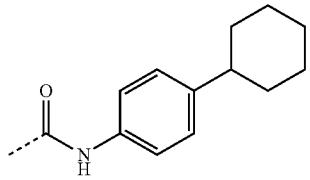 |  |  | H | >1000 |
| 13 | 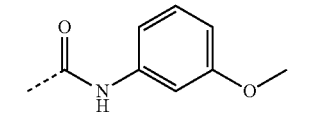 |  |  | PO$_3$H$_2$ | 90 |
| 14 | 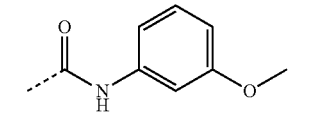 |  | 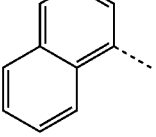 | PO$_3$H$_2$ | 28 |
| 15 | 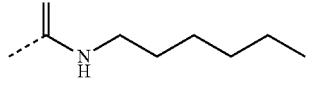 |  | 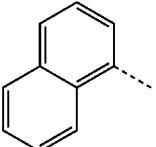 | PO$_3$H$_2$ | 58 |
| 16 | 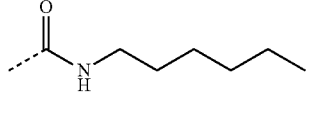 |  |  | PO$_3$H$_2$ | 25 |

TABLE 1-continued

IC$_{50}$ values (μM) for the inhibition of STAT3 DNA-binding activity in vitro via oxazole and thiazole analogs of ISS610.

Figure 6:
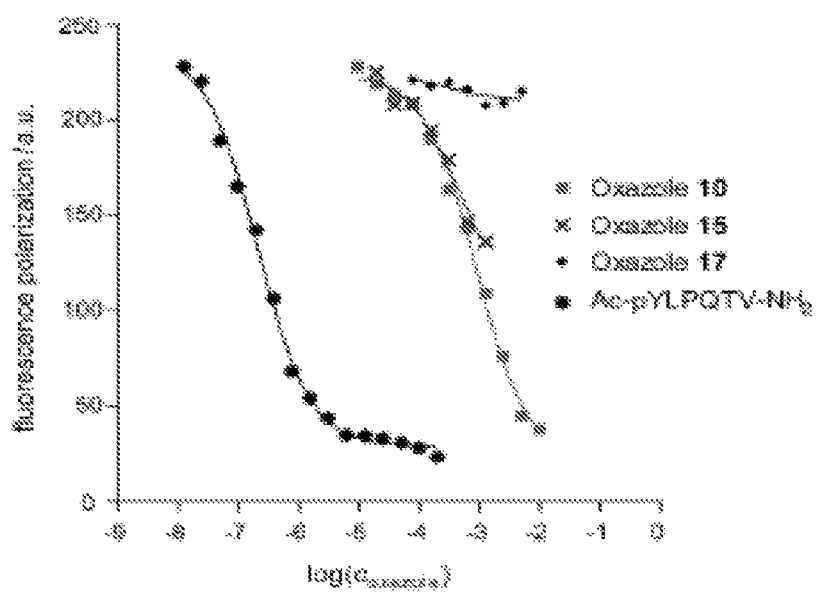
FIG. 6 is a line graph illustrating results of a competitive binding experiment between the fluorescent probe 5-carboxyfluorescein-GpYLPQTV-NH$_2$ and oxazoles 10, 15, 17 as well as unlabeled Ac-pYLPQTV-NH2 peptide to STAT3 protein; whereas Ac-pYLPQTV-NH2 displays a 200 nM affinity towards STAT3, and oxazole compounds 10, 15, and 17 do not interact significantly with STAT3.

| Compound Number | R$^1$ | R$^2$ | Scaffold Core | R$^3$ | IC$_{50}$ Values (μM)[a] |
|---|---|---|---|---|---|
| 17 | naphthyl | 4-(cyclohexyl)phenyl-NHC(O)- | oxazole | PO$_3$H$_2$ | 255 |
| 18 | naphthyl | 4-(cyclohexyl)phenyl-NHC(O)- | thiazole | PO$_3$H$_2$ | 350 |
| 19 | naphthyl | 3-methoxyphenyl-NHC(O)- | thiazole | PO$_3$H$_2$ | 125 | where X = O or S
[a]Inhibitor concentration required to decrease STAT3-DNA binding twofold.

unphosphorylated STAT3 monomer (10 and 15, Ki~1 mM; FIG. 6). These results were attributed to the smaller size of the oxazole scaffolds relative to the phosphopeptide, which is predicted to make contacts with both the BG and EF loops that recognize ligand residues at the pTyr+3 site. Structural limitations of the inhibitors might preclude effective interactions with the SH2 domain and reduce their ability to displace the extended peptide sequence.

Despite the inherent difficulties associated with the cell permeability of phosphate derivatives, promising whole-cell activities were observed for several lead compounds. Initial in vitro whole-cell experiments were conducted against normal mouse NIH-3T3 fibroblasts and v-src-transformed counterparts (NIH-3T3/v-src) that harbor aberrant STAT3. Inhibitor effects upon cell viability, proliferation, and cytotoxicity were assessed through WST-1, a cell proliferation reagent that measures the metabolic activity of viable cells. The most potent in vitro inhibitor, compound 10, displayed at least ten-fold selectivity toward malignant NIH-3T3/v-src fibroblasts with aberrant STAT3 (EC$_{50}$=120 μM) and negligible effects toward normal NIH-3T3 fibroblasts, in which STAT3 pathways are tightly regulated. Conversely, the suppression by lead peptidomimetic ISS610 in whole cells required millimolar concentrations of inhibitor. It is assumed that the predominantly hydrophobic nature of these compounds facilitated successful permeation of the cell membrane despite the phosphate.

In addition, cell-based EC$_{50}$ values were determined for potent inhibitors against human breast (MDA-MB-231) cancer cell lines (Table 2). Oxazole 10 had the best activity against breast cancer (EC$_{50}$=180 μM) and NIH-3T3/v-src cells (EC$_{50}$=120 μM) and lacked toxicity for control NIH-3T3 cells.

In summary, herein are disclosed the first rationally designed small-molecule inhibitors of STAT3 dimerization that disrupt STAT3-mediated cell proliferation pathways. Suitably substituted oxazole and thiazole scaffolds, derived from peptidomimetic leads, disrupted STAT3:STAT3-DNA-binding activity in vitro at low micromolar concentrations, but showed low affinity to the unphosphorylated STAT3 monomer. This might suggest that the present compounds preferentially bind with activated STAT3, a hypothesis which is further supported by the lack of activity against control cells (NIH-3T3); however, this remains to be verified. Lead agents showed potency and specific human cancer cell lines and negligible toxicity towards normal NIH-3T3 fibroblasts. The present studies highlight the widely acknowledged belief that STAT3 is a potent target for disruption by small-molecule inhibitors for novel anticancer drug development and that targeting of STAT3 will require yet a further level of investigation.

TABLE 2

EC$_{50}$ values for selected inhibitors against constitutively activated STAT3 containing cell lines NIH3T3/vSrc, Panc-1, MDA-231 and non-activated STAT3 NIH3T3 cells.

| Compound No. | Panc-1 EC$_{50}$ (μM) | MDA-231 EC$_{50}$ (μM) | NIH3T3 EC$_{50}$ (μM) | NIH3T3/vSrc |
|---|---|---|---|---|
| 10 | >1000 | 180 | >1000 | 120 |
| 14 | >1000 | >1000 | >1000 | 480 |
| 16 | >1000 | 300 | >1000 | 145 |
| 19 | 10 | >1000 | >1000 | 700 |

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A compound having a chemical structure according to the formula:

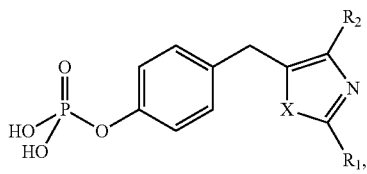

wherein X is oxygen or sulfur, R$^1$ is a phenyl group or a naphthyl group, and R$^2$ is an amide group, wherein the compound is not:

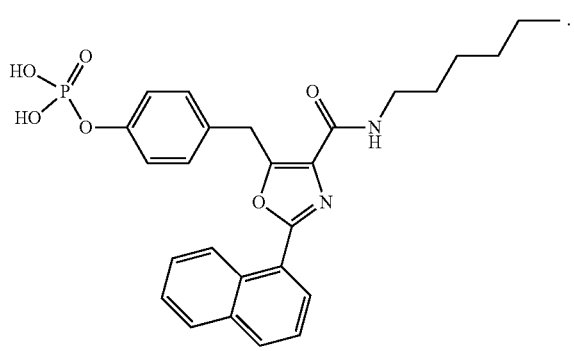 [SMILES: CCCCCCNC(=O)c1nc(-c2cccc3ccccc23)oc1Cc1ccc(OP(=O)(O)O)cc1]

2. A pharmaceutically acceptable salt of the compound of claim 1.
3. A pharmaceutically acceptable composition containing the compound of claim 1 or a salt thereof.
4. The compound of claim 1, wherein X is oxygen.
5. The compound of claim 1, wherein X is oxygen, and R$^2$ is an amide group selected from:

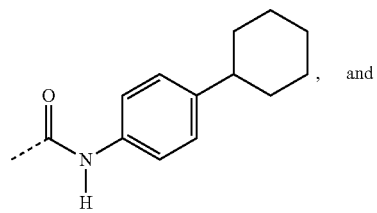, and

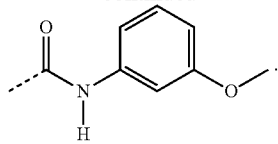

6. The compound of claim 1, wherein X is sulfur.
7. The compound of claim 1, wherein X is sulfur, and R$^2$ is an amide group selected from:

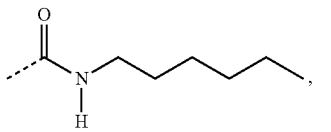,

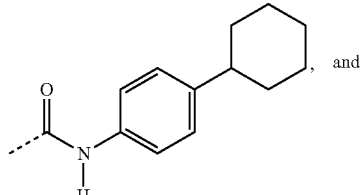, and

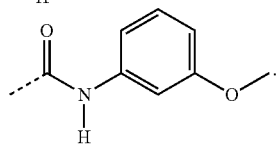

8. The compound of claim 1, wherein R$^1$ is a phenyl group.
9. The compound of claim 1, wherein, R$^1$ is a naphthyl group.
10. The compound of claim 1, selected from:

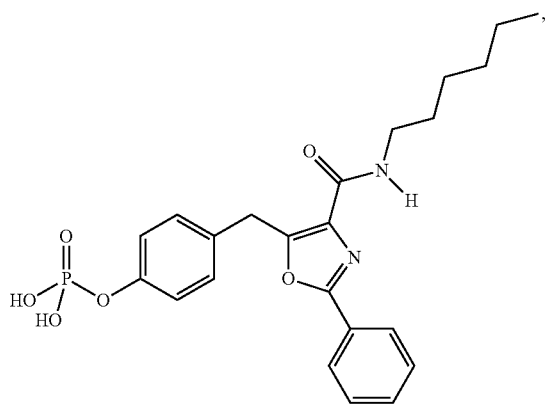

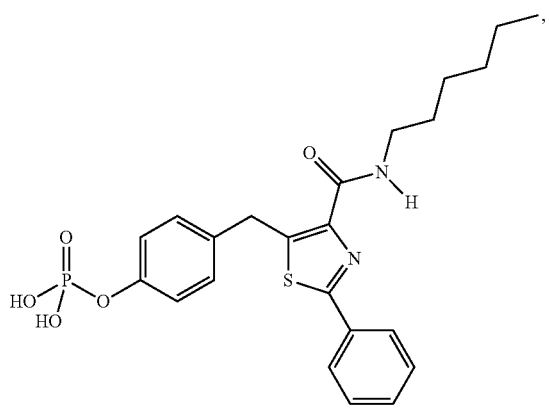

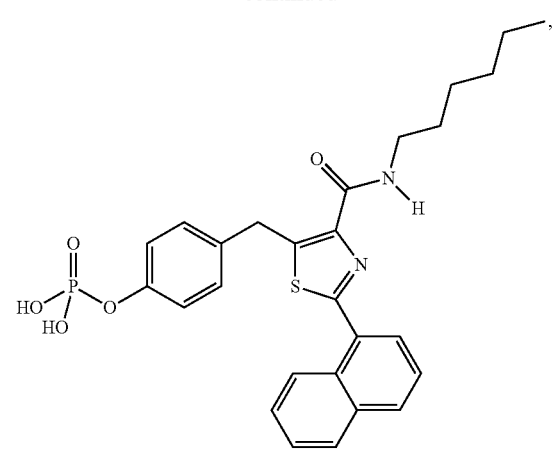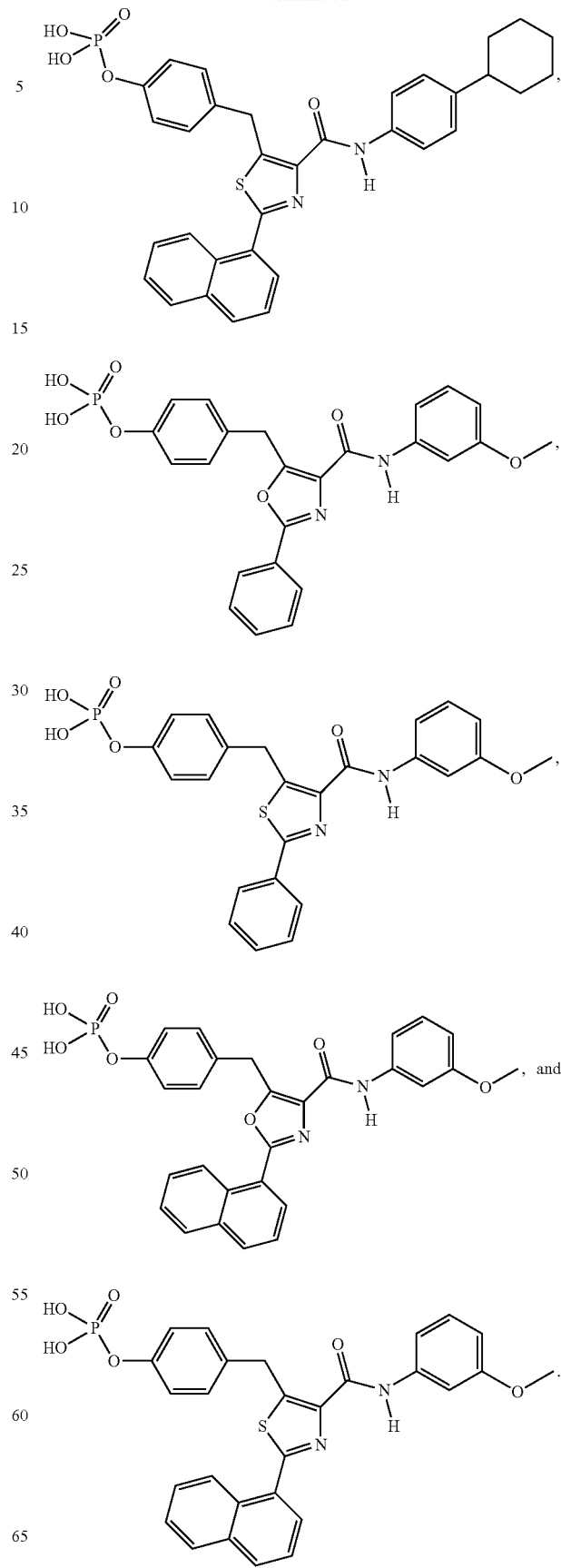

11. The compound of claim 1, selected from:

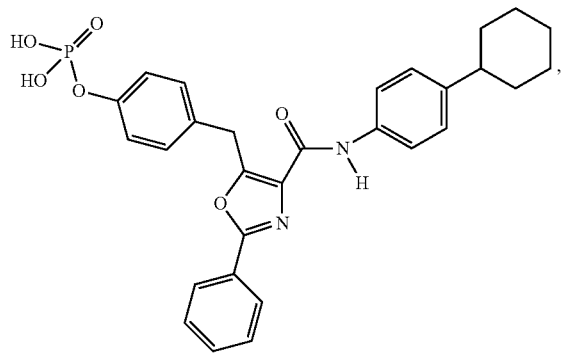

and

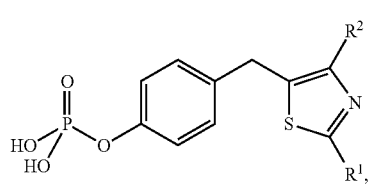

12. A compound having a chemical structure according to the formula:

wherein $R^1$ is a phenyl group or a naphthyl group, and $R^2$ is an amide group.

13. A pharmaceutically acceptable salt of the compound of claim 12.

14. A pharmaceutically acceptable composition containing the compound of claim 12 or a salt thereof.

15. The compound of claim 12, wherein $R^1$ is a phenyl group.

16. The compound of claim 12, wherein $R^2$ is an amide group selected from:

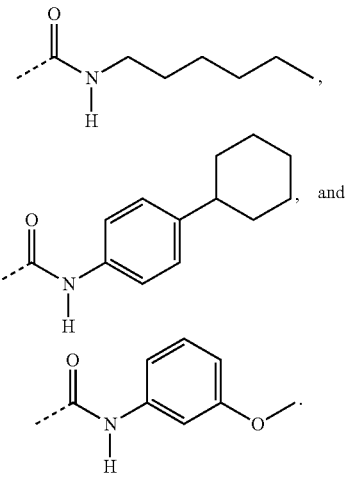

17. The compound of claim 12, selected from:

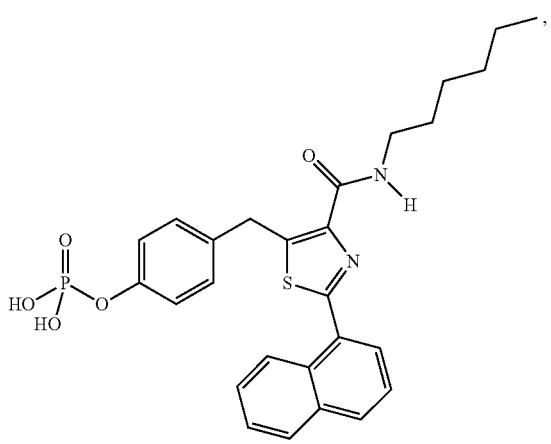

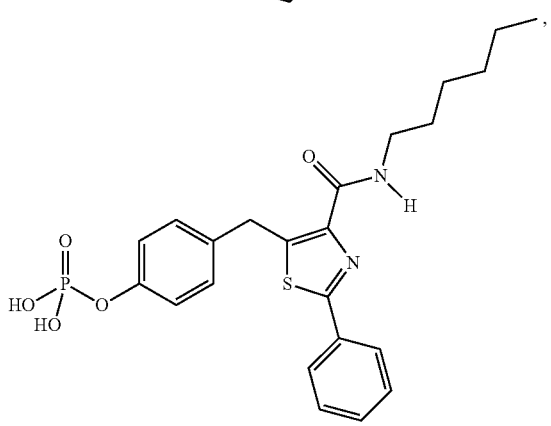

-continued

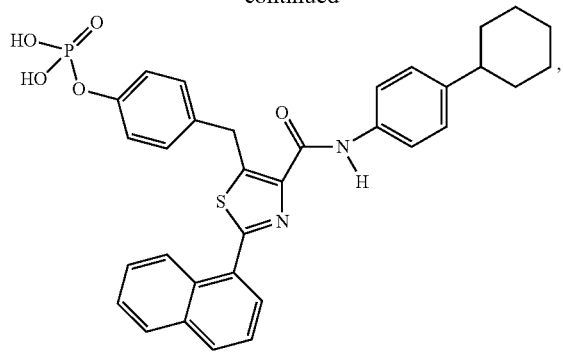

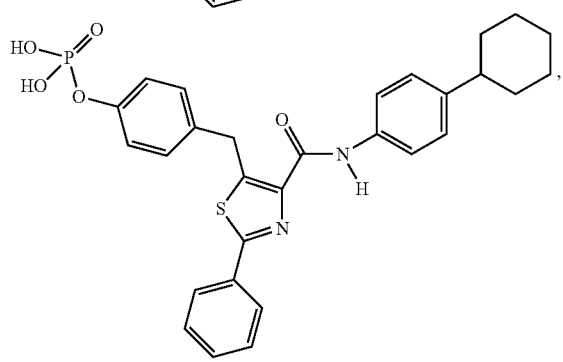

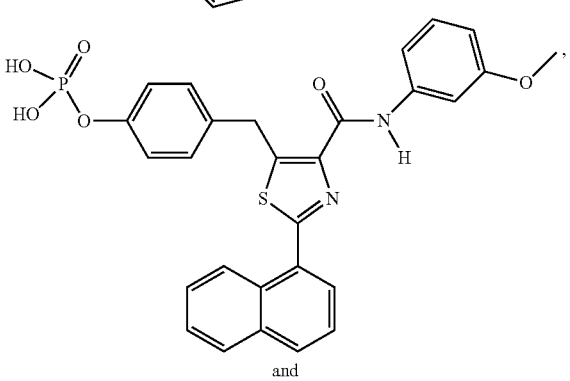

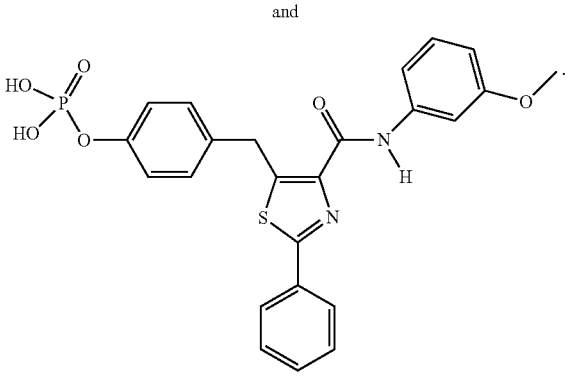

18. A compound having a chemical structure according to the formula:

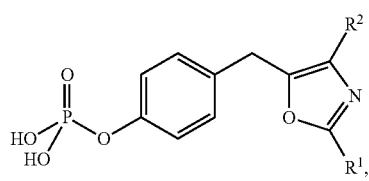

wherein $R^1$ is a phenyl group or a naphthyl group, and $R^2$ is an amide group selected from:

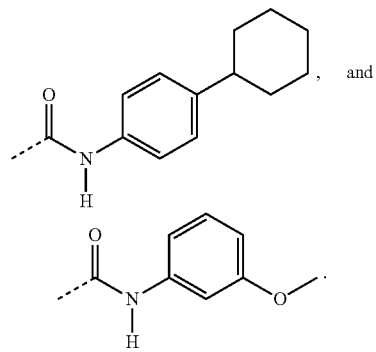

19. A pharmaceutically acceptable salt of the compound of claim 18.

20. A pharmaceutically acceptable composition containing the compound of claim 18 or a salt thereof.

21. The compound of claim 18, wherein $R^1$ is a phenyl group.

22. A compound having a chemical structure according to the formula:

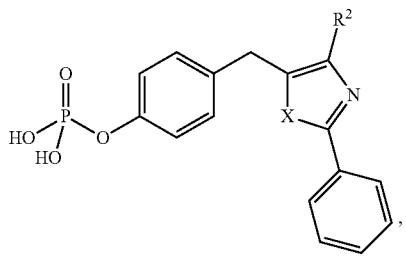

wherein X is oxygen or sulfur, and $R^2$ is an amide group.

23. A pharmaceutically acceptable salt of the compound of claim 22.

24. A pharmaceutically acceptable composition containing the compound of claim 22 or a salt thereof.

25. The compound of claim 22, wherein X is sulfur.

26. The compound of claim 22, wherein $R^2$ is an amide group selected from:

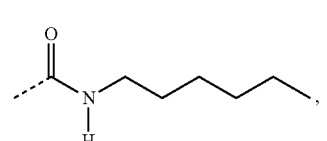

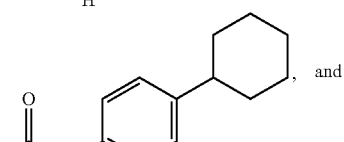

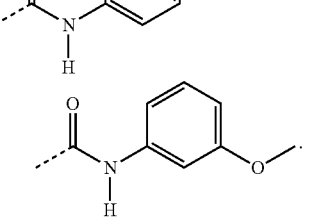

27. The compound of claim 22, selected from:

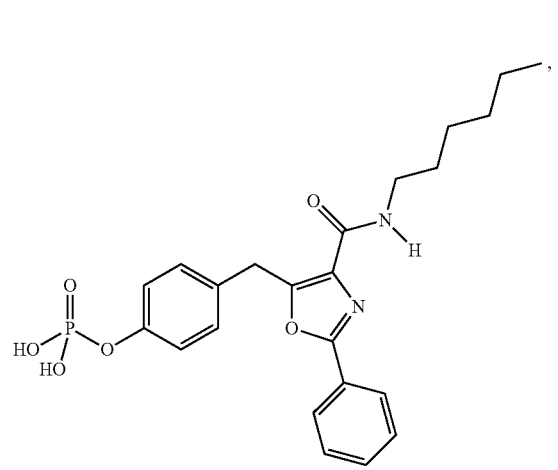

,

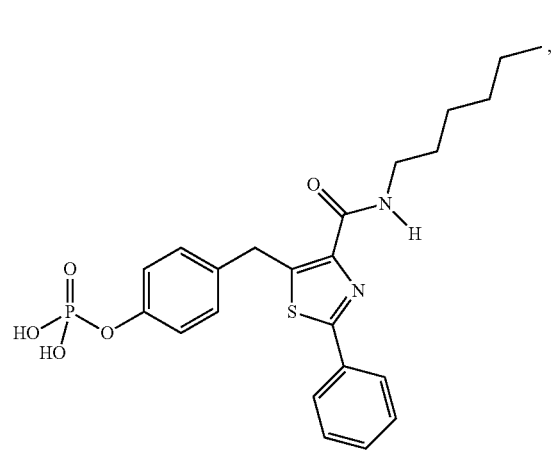

,

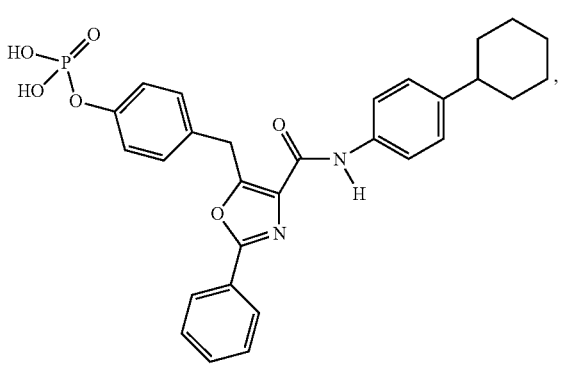

,

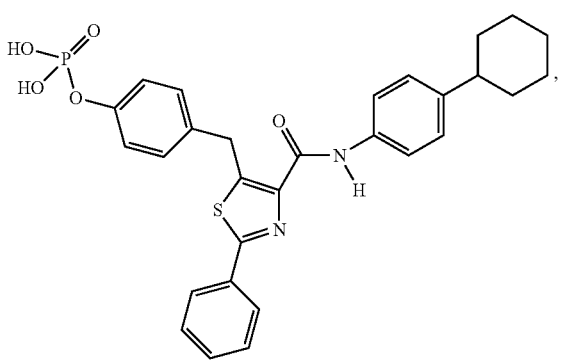

,

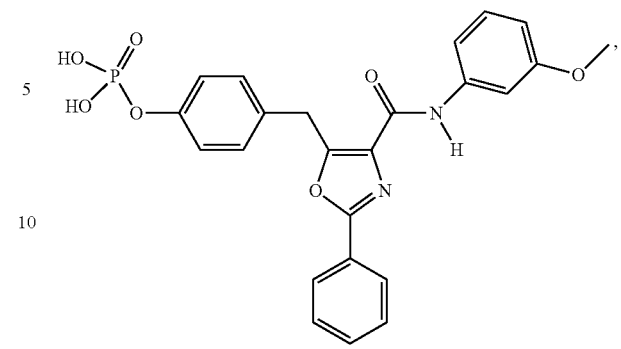

and

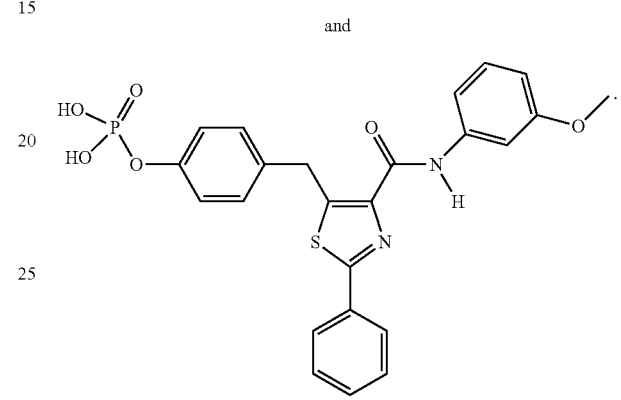

28. A compound having a chemical structure according to the formula:

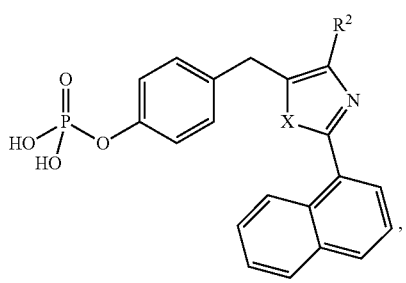

, wherein X is oxygen or sulfur, and $R^2$ is an amide group selected from:

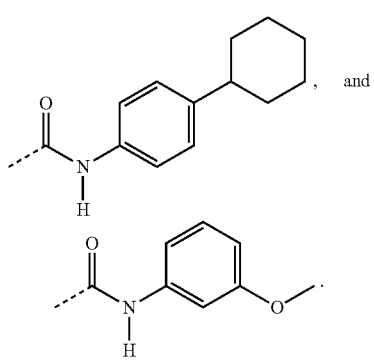

29. A pharmaceutically acceptable salt of the compound of claim 28.

30. The compound of claim 28, wherein X is sulfur.

31. A pharmaceutically acceptable composition containing the compound of claim 28 or a salt thereof.

32. The compound of claim 28, selected from:

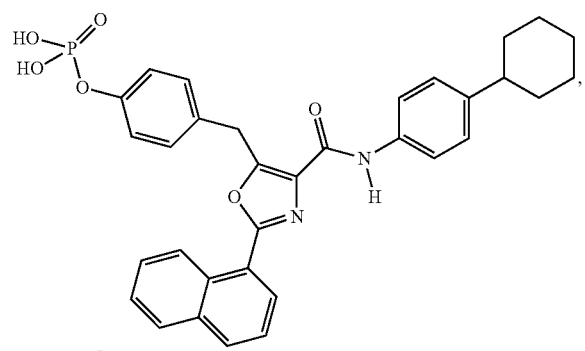

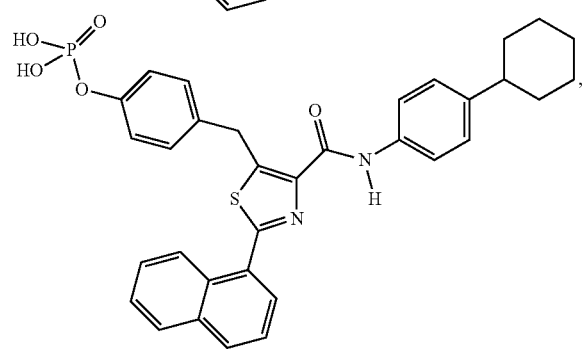

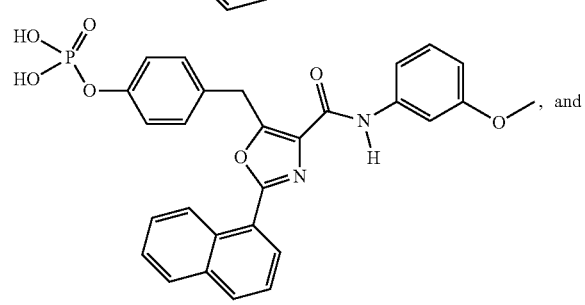

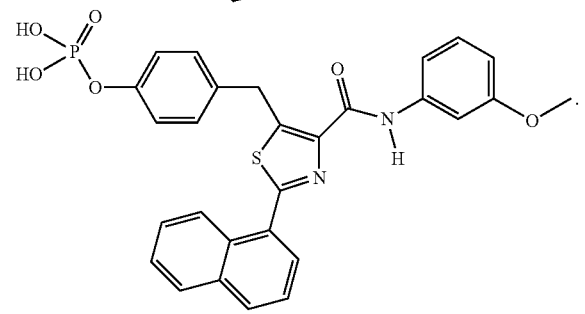

33. A compound having a chemical structure according to the formula:

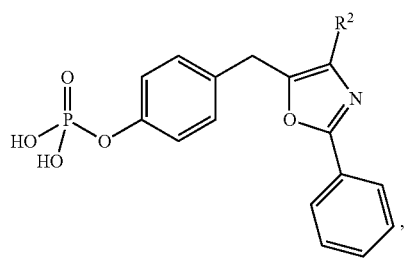

wherein $R^2$ is an amide group.

34. A pharmaceutically acceptable salt of the compound of claim 33.

35. A pharmaceutically acceptable composition containing the compound of claim 33 or a salt thereof.

36. The compound of claim 33, wherein $R^2$ is an amide group selected from:

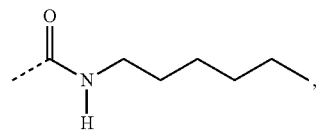

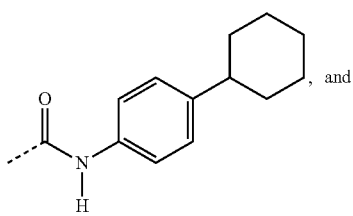

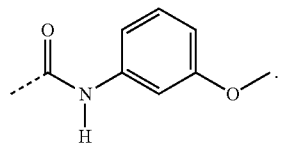

37. The compound of claim 33, selected from:

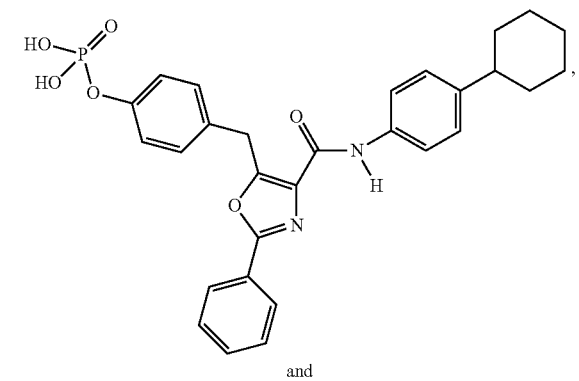

-continued

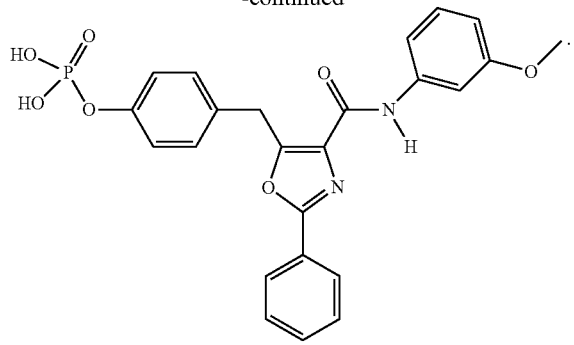

38. A compound having a chemical structure according to the formula:

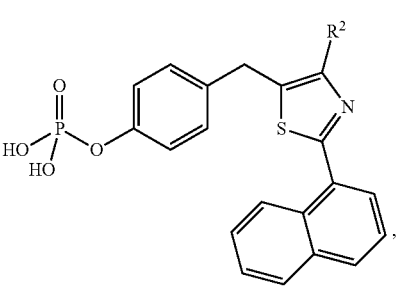

wherein R² is an amide group.

39. A pharmaceutically acceptable salt of the compound of claim 38.

40. A pharmaceutically acceptable composition containing the compound of claim 38 or a salt thereof.

41. The compound of claim 38, wherein R² is an amide group selected from:

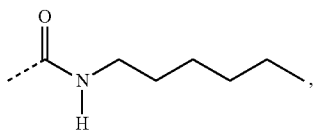

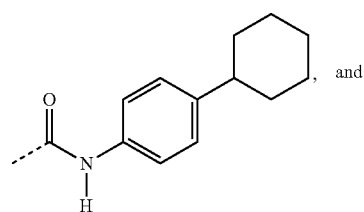

-continued

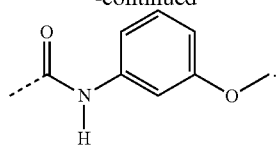

42. The compound of claim 38, selected from:

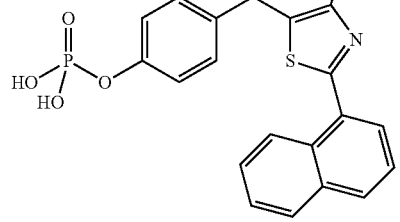

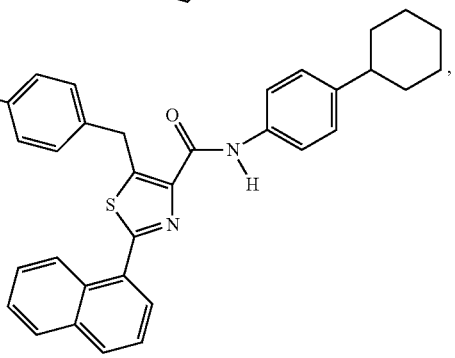

and

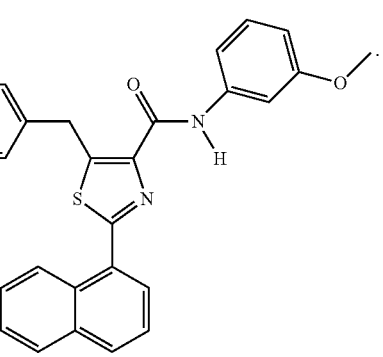

* * * * *